US007226914B2

(12) United States Patent
Zaneveld et al.

(10) Patent No.: US 7,226,914 B2
(45) Date of Patent: Jun. 5, 2007

(54) CELLULOSE SULFATE AND OTHER SULFATED POLYSACCHARIDES TO PREVENT AND TREAT PAPILLOMA VIRUS INFECTION AND OTHER INFECTIONS

(75) Inventors: Lourens J. D. Zaneveld, Chicago, IL (US); Robert A. Anderson, Chicago, IL (US); Thomas C. Usher, Point Roberts, WA (US)

(73) Assignees: Rush Presbyterian-St. Luke's Medical Center, Chicago, IL (US); Polydex Pharmaceuticals Limited, Nassau (BS)

( * ) Notice: Subject to any disclaimer, the term of this patent is extended or adjusted under 35 U.S.C. 154(b) by 0 days.

(21) Appl. No.: 11/001,412

(22) Filed: Dec. 1, 2004

(65) Prior Publication Data

US 2005/0203055 A1     Sep. 15, 2005

Related U.S. Application Data

(62) Division of application No. 10/312,030, filed as application No. PCT/CA01/00964 on Jun. 29, 2001.

(60) Provisional application No. 60/215,325, filed on Jun. 30, 2000.

(51) Int. Cl.
*A61K 31/715* (2006.01)
*A61K 31/727* (2006.01)
(52) U.S. Cl. ............................. 514/54; 514/53; 514/55; 514/56; 514/57; 514/58; 514/59
(58) Field of Classification Search ................ 514/54, 514/53, 55, 56, 57, 58, 59
See application file for complete search history.

(56) References Cited

U.S. PATENT DOCUMENTS

| | | | | |
|---|---|---|---|---|
| 4,840,941 | A | * | 6/1989 | Ueno et al. ................... 514/59 |
| 5,208,031 | A | | 5/1993 | Kelly .......................... 424/412 |
| 5,288,704 | A | | 2/1994 | Ungheri et al. ............... 514/12 |
| 5,853,767 | A | | 12/1998 | Melman ...................... 424/659 |
| 5,958,461 | A | | 9/1999 | Larsen ........................ 424/614 |
| 6,063,773 | A | | 5/2000 | Anderson et al. ............. 514/57 |
| 6,239,182 | B1 | | 5/2001 | Zaneveld et al. ........... 514/764 |

FOREIGN PATENT DOCUMENTS

| | | | |
|---|---|---|---|
| EP | 0 116 251 A1 | | 12/1983 |
| EP | 0 298 706 A2 | | 7/1988 |
| EP | 0 402 078 A2 | | 12/1990 |
| EP | 0 497 341 A2 | | 8/1992 |
| EP | 0676 206 A1 | | 10/1995 |
| FR | 2542616 A | * | 9/1984 |
| WO | WO 94/08574 | | 4/1994 |

OTHER PUBLICATIONS

Wang et al, "Heparin's anti-inflammatory effects require glucosamine 6-O-sulfation and are mediated by blockade of L- and P-selectins", The Journal of Claincal Investigation, Jul. 2002, vol. 110, No. 1, pp. 127-136.*

Saggau, D. D. et al. "Replication of Fungi in K-Sol Corneal Preservation Medium at 4° C". Archives of Ophthalmology, vol. 104, Sep. 1986, 1362-1363.

Klotz, S. A. et al. "Glycosaminoglycans inhibit *Cadida albican* adherence to extracellular matrix proteins". FEMS Microbiology Letters, (1992), 205-208.

Tzenan Giroglou, et al. *Human Papillomavirus Infection Requires Cell Surface Heparan Sulfate* Journal of Virology, Feb. 2001, p. 1565-1570.

Pisani, P., et al. *Estimates of the worldwide mortality from eighteen major cancers in 1985. Implications for prevention and projections of future burden.* International Journal of Cancer 55:891-903. 1993.

Christensen, N. D., et al. 1995. *Postattachment neutralization of papillomaviruses by monoclonal and polyclonal antibodies.* Virology 207:136-142.

Christensen, N. D., et al 1990. *Monoclonal antibody-mediated neutralization of infectious human papillomavirus type 11.*J.Virol. 64:5678-5681.

Sokal, D. C., et al. 1995. *Inactivation of papillomavirus by low concentrations of povidone-iodine.* Sex. Transm. Dis. 22:22-24.

Howett, M. K., et al. 1999. *A broad-spectrum microbicide with virucidal activity against sexually transmitted viruses.* Antimicrob. Agents Chemother. 43:314-321.

Howett, M. K., et al. *Alkyl sulfates: a new family of broad spectrum microbicides.* XIII International AIDS Conference, 707-712. 2000. Durban, South Africa, Monduzzi Editore.

Yamamoto et al., *Carbohydrate Polymers* 14 (1990) 53-63.

Dvoretzky, I., et al. 1980. *A quantitative in vitro focus assay for bovine papilloma virus.* Virology 103:369-375.

Smith, L. H. et al. 1993. *In vitro HPV-11 infection of human foreskin.* J.Invest.Dermatol. 101:292-295.

Ludmerer, S. W., et al. 2000. *HPV11 mutant virus-like particles elicit immune Responses that neutralize virus and delineate a novel neutralizing domain.* Virology 266:237-245.

Smith, L. H., et al. 1995. *Titration of HPV-11 infectivity and antibody neutralization can be measured in vitro.* J.Invest.Dermatol. 105:438-444.

Zeitlin, I., et al., (2001) *Tests of BufferGel for Contraception and Prevention of Sexually Transmitted Diseases in Animal Models.* Sex. Trans. Dis. (July) 28: 417-423.

Christensen, N.D., et al., *Papillomavirus microbial activities of high-molecular-weight cellulose sulfate, dextran sulfate and polystyrene sulfonate.* Antimicrobial Agents and Chemotherapy, Dec. 2001, 45:3427-3432.

(Continued)

*Primary Examiner*—Shaojia Anna Jiang
*Assistant Examiner*—Everett White
(74) *Attorney, Agent, or Firm*—Arnold B. Silverman; Eckert Seamans Cherin & Mellott, LLC

(57) ABSTRACT

A method for treating and preventing various infections, including papilloma virus and fungal and parasitic infections is provided. In particular, an effective amount of a sulphated polysaccharide, such as cellulose sulphate and dextran sulphate are administered to prevent and treat these infections. The invention also relates to use of these compounds for the prevention and inhibition of malignant epithelial lesions associated with papilloma virus, such as cervical cancer.

30 Claims, No Drawings

OTHER PUBLICATIONS

Anderson, R.A., et al. *Preclinical Evaluation of Sodium Cellulose Sulfate (Ushercell) as a Contraceptive Antimicrobial Agent.* Journal of Andrology, Jun. 2002, 23:426-438.

Simoes, et al., *Two Novel Vaginal Microbicides (Polystyrene Sulfonate and Cellulose Sulfate) Inhibit Gardnerella vaginalis and Anaerobes Commonly Associated with Bacterial Vaginosis.* Antimicrobial Agents and Chemotherapy, Aug. 2002, vol. 46, No. 8, p. 2692-2695.

Joyce, et al. *The L1 Major Capsid Protein of Human Papillomavirus Type 11 Recombinant Virus-like Particles Interacts with Heparin and Cell-surface Glycosaminoglycans on Human Keratinocytes.* The Journal of Biological Chemistry, 1999, vol. 274, No. 9, Feb. 26, pp. 5810-5822.

Hermonat, et al. *The spermicide nonaxynol-9 does not inactivate papillomavirus* Sex. Transm. Dis. 1992; 19:203-205.

* cited by examiner

CELLULOSE SULFATE AND OTHER SULFATED POLYSACCHARIDES TO PREVENT AND TREAT PAPILLOMA VIRUS INFECTION AND OTHER INFECTIONS

CROSS-REFERENCE TO RELATED APPLICATIONS

The present application is a divisional of U.S. Ser. No. 10/312,030 filed Dec. 19, 2002, which was a 371 of PCT/CA01/00964 field Jun. 29, 2001 which, in turn, claimed the benefit of U.S. Provisional Application 60/215,325 filed Jun. 30, 2000.

FIELD OF THE INVENTION

This invention relates to prevention and treatment of various infectious agents and in particular, relates to inhibitory activity of cellulose sulfate and other sulfated polysaccharides against various infectious agents, including papilloma virus and various vaginitis-causing microbes.

BACKGROUND

U.S. Pat. No. 4,840,941 (941) describes inhibitory effects of certain sulfated polysaccharides on the enveloped retrovirus, human T-cell lymphotrophic virus-III (now known as HIV-1 (human immunodeficiency virus-1)). As disclosed in U.S. Pat. No. 5,288,704, sulfated polysaccharides are also known to be effective against various other enveloped viruses and in particular herpes simplex virus (HSV). The 941 patent, however, discloses that the inhibitory characteristics of sulfated polysaccharides against HIV-1 is quite different from the activities of polysaccharide sulfates against herpes virus. Since different viruses can have fundamentally different properties, a sulfated polysaccharide which is effective against one virus may not be effective against a different virus.

While the binding of human papilloma virus-like particles (VLP's) to HaCaT cells has been shown to be inhibited by heparin and dextran sulfate (Joyce et al. *The L1 Major Capsid Protein of Human Papillomavirus Type* 11 *Recombinant Virus-like Particles Interacts with Heparin and Cell-surface Glycosaminoglycans on Human Keratinocytes.* The Journal of Biological Chemisty, 1999, Vol 274, No. 9, February 26, pp. 5810-5822), studies with VLP's do not reflect papilloma virus infection and it is not known that sulfated polysaccharides can inhibit papilloma virus infection. Papilloma virus differs from HSV and HIV in that it does not have an envelope and it differs from retroviruses such as HIV since it is a DNA virus and does not rely on the enzyme reverse transcriptase for replication. This difference may explain the resistance of papilloma virus to nonoxynol-9, a commonly used spermicide, which has been shown to inhibit both HIV and HSV (Hermonat, P. L., Daniel, R. W. and Shah, K. V. *The spermicide nonoxynol-*9 *does not inactivate papillomavirus* Sex. Transm. Dis. 1992; 19:203-205).

Papilloma viruses infect basal cells of epithelia and induce squamous epithelial and fibroepithelial tumors, e.g., warts (papillomas) and condylomata and can lead to malignant epithelial lesions. (Tzenan Giroglou, et al. *Human Papillomavirus Infection Requires Cell Surface Heparan Sulfate* Journal of Virology, February 2001, p. 1565-1570). Genital human papilloma virus infections represent one of the most frequent sexually transmitted diseases (STDs) and papilloma virus infection of the vaginal mucosa in women has been linked to cervical cancer. Cervical cancer represents the second most frequent cause of cancer-related deaths in women and accounts for more than 200,000 deaths per year world-wide (Pisani, P., Parkin, D. M., and Ferlay, J. *Estimates of the worldwide mortality from eighteen major cancers in* 1985. *Implications for prevention and projections of future burden.* International Journal of Cancer 55:891-903. 1993).

To date, very few reagents with microbicidal activity against human papilloma virus (HPV) infections have been described. These include reagents that specifically target HPVs such as monoclonal antibodies with virus neutralizing activity (Christensen, N. D., N. M. Cladel, and C. A. Reed. 1995. *Postattachment neutralization of papillomaviruses by monoclonal and polyclonal antibodies.* Virology 207:136-142; Christensen, N. D., J. W. Kreider, N. M. Cladel, S. D. Patrick, and P. A. Welsh. 1990. *Monoclonal antibody-mediated neutralization of infectious human papillomavirus type* 11. J. Virol. 64:5678-5681) and virus non-specific agents such as povidone-iodine (Sokal, D. C. and P. L. Hermonat. 1995. *Inactivation of papillomavirus by low concentrations of povidone-iodine.* Sex Transm. Dis. 22:22-24.), alkyl sulfates and monocaprin (Howett, M. K, E. B. Neely, N. D. Christensen, B. Wigdahl, F. C. Krebs, D. Malamud, S. D. Patrick, M. D. Pickel, P. A. Welsh, C. A. Reed, M. G. Ward, L. R. Budgeon, and J. W. Kreider. 1999. *A broad-spectrum microbicide with virucidal activity against sexually transmitted viruses.* Antimicrob. Agents Chemother. 43:314-321; Howett, M. K., Wigdahl, B., Malamud, D., Christensen, N. D., Wyrick, P. B., Krebs, F. C., and Catalone, B. J. *Alkyl sulfates: a new family of broad spectrum microbicides.* XIII International AIDS Conference, 707-712. 2000. Durban, South Africa, Monduzzi Editore). Several reagents that have microbicidal activity against a broad range of STDs have proven to be ineffective against papillomaviruses such as C31G and as mentioned above nonoxynol-9. Some of these agents also induce significant cellular cytotoxicity. An effective treatment or prevention of papilloma virus infection is currently not available.

Cellulose sulfate, a sulfated polysaccharide can be synthesized by various known methods of sulfation of cellulose and may be readily obtained commercially. Sulfated cellulose has been reported to inhibit HIV activities in vitro (Yamamoto et al., Carbohydrate Polymers 14 (1990) 53-63). U.S. Pat. No. 6,063,773 (773) discloses the inhibitory effects of cellulose sulfate on HIV and HSV and further discloses that it can be used to treat or prevent bacterial infections. The 773 patent also discloses cellulose sulfate can reduce the risk of conception.

SUMMARY OF THE INVENTION

The present invention is based in part on the unexpected finding that cellulose sulfate is effective against papilloma virus infection and against other infections including those associated with fungal and parasitic vaginitis. Cellulose sulfate is also effective against many vaginosis-causing bacteria.

In one aspect, the present invention relates to a method of preventing, inhibiting or treating an infection by papilloma virus in a subject in need of such prevention, inhibition or treatment comprising administering an effective amount of a sulfated polysaccharide such as cellulose sulfate and dextran sulfate. In another aspect, the invention relates to a method of preventing or inhibiting a malignant epithelial lesion, including cervical cancer, in a subject in need of such prevention or inhibition comprising administering an effective amount of a sulfated polysaccharide such as cellulose sulfate and dextran sulfate. In other aspects, the invention relates to a method of preventing, inhibiting or treating other infections, including fungal and parasitic infections, such as for example by *Trichomonas vaginalis, Aspergillus niger* and *Candida albicans,* in a patient in need of such prevention, inhibition and treatment comprising administering an effective amount of a sulfated polysaccharide such as cellulose sulfate.

The present invention also relates to use of an effective amount of a sulfated polysaccharide such as cellulose sulfate and dextran sulfate for preventing, inhibiting or treating an infection by papilloma virus in a subject in need of such prevention, inhibition or treatment. In another aspect, the invention relates to use of an effective amount of a sulfated polysaccharide such as cellulose sulfate and dextran sulfate for preventing or inhibiting a malignant epithelial lesion, including cervical cancer, in a subject in need of such prevention or inhibition. In other aspects, the invention relates use of an effective amount of a sulfated polysaccharide such as cellulose sulfate for preventing, inhibiting or treating other infections, including fungal and parasitic infections, such as for example by *Trichomonas vaginalis, Aspergillus niger* and *Candida albicans,* in a patient in need of such prevention, inhibition and treatment

DETAILED DESCRIPTION OF THE INVENTION

It has been found that cellulose sulfate and dextran sulfate are effective in inhibiting infection by papilloma virus and against fungal and parasitic infections including those associated with vaginitis. Cellulose sulfate is also effective against many vaginosis-causing bacteria. A sulfated polysaccharide such as cellulose sulfate and dextran sulfate therefore can be used to prevent, inhibit or treat infections caused by these organisms. Moreover, since papilloma virus infection is associated with malignant epithelial lesions, including cervical cancer, a sulfated polysaccharide such as cellulose sulfate or dextran sulfate, by preventing papilloma virus infection can also prevent these lesions, including cervical cancer. Moreover, since these compounds can effectively inactivate papilloma virus, they can inhibit these lesions, including cervical cancer by inhibiting the spread of the infectious agent.

Cellulose sulfate of a wide range molecular weight (Mr) may be used. In one embodiment, cellulose sulfate of average Mr greater than about 500,000 daltons may be used. In another embodiment, cellulose sulfate of average Mr of about 1-2 million daltons may be used. The degree of sulfation of cellulose sulfate is preferably above 12% and most preferably about 17-18% which represents maximal sulfation. Cellulose sulfate in the form of a pharmaceutically acceptable salt, for example sodium cellulose sulfate may also be used. Other pharmaceutically acceptable salts include, among others, potassium, lithium and ammonium cellulose sulfate.

Cellulose sulfate in an effective amount may be administered in a suitable dosage form, depending on the site of administration. An "effective amount" refers to an amount effective at dosages and for periods of time necessary to achieve the desired therapeutic result, such as to prevent or inhibit infections by papilloma virus or other microbes. The effective amount may vary according to various factors such as the infection being treated, disease state, age, sex and weight of the individual being treated. While the effective amount can be readily determined, the studies to date suggest that best results may be achieved with about 0.1 to 200 mg/ml of cellulose sulfate, preferably 1 to 100 mg/ml and more preferably 50 to 100 mg/ml.

An effective amount of cellulose sulfate may be administered to the area or areas that have or are expected to come into contact with the infectious agent. For example, to prevent, inhibit or treat vaginal infections, or to prevent or inhibit cervical cancer, cellulose sulfate may be administered as gels, foams, suppositories, creams or aerosols into the vaginal cavity using appropriate applicators. In the case of a sexually transmitted infection such as papilloma virus infection, cellulose sulfate may also be administered to the rectum, or using suitable edible capsules and flavouring agents, to the mouth, or to the vaginal cavity, of one or more sexual partners, whether known to be infected or not, to prevent or inhibit transmission during vaginal or anal intercourse or oral sex. Cellulose sulfate may be administered prior to, during or after sexual activity, providing further flexibility and ease of use. If administered after sexual activity, best results may be achieved immediately following the sexual activity. To prevent, inhibit or treat skin infection, for example, caused by fungal infection, including by *Candida albicans,* or to prevent or inhibit malignant epithelial lesions, cellulose sulfate may be topically applied to the skin for example as a cream or gel. Cellulose sulfate may also be administered as an oral dosage form, for example, in the form of a tablet.

Suitable carriers or diluents known to those skilled in the art may be combined in the preparation of a suitable dosage form and patients receiving the treatment may be monitored for its effectiveness in the known manner.

In the case of a gel, cellulose sulfate may be combined with glycerin and suitable preservatives such as methylparaben and propylparaben. Other suitable excipients may also be added, for example, a thickening agent, such as hydroxyethylcellulose. If cellulose sulfate is used on the skin, it may simply be mixed in water, saline or a buffering solution and applied as a gel.

Phase I Safety Study indicates that cellulose sulfate which is noncytotoxic is better tolerated than nonoxynol-9, a cytotoxic agent frequently found in spermicidal gels, and as well as or even better than K-Y Jelly, a lubricant. Cellulose sulfate offers a further advantage in that irritation by a cytotoxic agent can cause lesions which may facilitate infection and the use of cellulose sulfate is not associated with such risks of infection.

Dextran sulfate of a wide range of Mr, may be administered as described for cellulose sulfate in similar dosage forms. In one embodiment, dextran sulfate of average Mr greater than about 500,000 may be used. In another embodiment, the Mr may be about 1-2 million. The effective amount may vary according to various factors, including those already described and may be readily determined. In one embodiment, about 0.1 to 200 mg/ml of dextran may be administered, preferably about 1 to 100 mg/ml and more preferably, 50 to 100 mg/ml.

While the use or administration of cellulose sulfate and dextran sulfate according to the invention have been described, other sulfated polysaccharides may be similarly administered in similar dosage forms in accordance with the invention. Preferably, the sulfated polysaccharide has a Mr ranging from about 15000 to 3,000,000. Preferably, the Mr is greater than about 500,000. The polysaccharide can be a homo-or heteropolysaccharide, preferably a homopolysaccharide, as are cellulose sulfate and dextran sulfate, with monomeric units consisting of either aldo-, deoxyaldo-, keto- or deoxyketopentoses, including, but not restricted to, arabinose, ribose, deoxyribose, galactose, fructose, sorbose, rhamnose and fucose, joined by either alpha- or beta-linkages. The polymer can be linear or branched, with free hydroxyl groups of the monomeric units maximally or partially sulfated. Preferably, the hydroxyl groups are maximally sulfated. The monomeric units may be further modified by the presence of carboxyl, amino and ester groups. Examples of suitable sulfated polysaccharides include dermatan sulfate, chondroitin sulfate, pentosan sulfate, fucoidin, mannan sulfate, carrageenan, dextrin sulfate, curdlan sulfate, chitin sulfate, heparin and heparin sulfate all of which may be obtained commercially.

The terms, cellulose sulfate, dextran sulfate, dermatan sulfate, chondroitin sulfate, pentosan sulfate, fucoidin, mannan sulfate, carrageenan, dextrin sulfate, curdlan sulfate, and chitin sulfate are intended include within their scope pharmaceutically acceptable salts thereof. Similarly, the term sulfated polysaccharides include within its scope pharmaceutically acceptable salts thereof. Moreover, while human patients are contemplated as subjects in need of prevention, inhibition or treatment according to the invention, other mammals susceptible to similar infection (and lesions in the case of infection by papilloma virus) are also subjects for such prevention, inhibition or treatment.

EXAMPLE 1

Inhibition of Bovine Papilloma Virus (BPV)

Cellulose sulfate was tested for its ability to inhibit BPV infection by cell focus formation assay (see Hermonat et al. (1992) for a description of this assay). The results are shown below. Cellulose sulfate from Dextran Products Limited (Lot 80971 in the form of sodium cellulose sulfate, known as Ushercell J.) was mixed with BPV type I (obtained from bovine fibropapillomas) prior to adding the virus to mouse fibroblast line C127 cells or mixed with these host cells first prior to adding the virus. In one molecular weight study, the $M_r$ range of cellulose sulfate was about 750 to 20.3 million, with an average $M_r$ of about 1.01 million. The peak $M_r$ as seen on HPLC was about 2.77 million. In another study, the average molecular weight was determined to be about 1.9 million with a peak $M_r$ of about 2.3 million. Unless otherwise specified, the $M_r$ is in daltons.

TABLE A

Inhibition of Bovine Papillomavirus type I by Cellulose sulfate

| | Method of Compound Exposure | |
|---|---|---|
| [Cellulose Sulfate] (µg/ml) | Pre-incubated with virus prior to addition to host cells Viral-induced foci per culture | Pre-incubated with host cells prior to addition to virus Viral-induced foci per culture |
| 0 | 450 | 450 |
|   | 450 | 450 |
| 5.0 | 121 | 72 |
|   | 97 | 60 |
| 50 | 37 | 10 |
|   | 32 | 12 |
| 500 | 0[A] | 0[A] |
|   | 0 | 0 |
| 5000 | 0[B] | 0[B] |
|   | 0 | 0 |

[A]Mild monolayer disruption
[B]Monolayer at approximately 80% confluency; disrupted The results indicate a dose response and the formation of oncogenic foci by the virus is completely inhibited at 500 µg/ml when cellulose sulfate is mixed with the virus or with the host cells.

The assay was repeated using different concentrations of cellulose sulfate and the results are shown below.

TABLE B

Inhibition of Bovine Papillomavirus type I by Cellulose sulfate

| | Method of Compound Exposure | |
|---|---|---|
| [Cellulose Sulfate] (µg/ml) | Pre-incubated with virus prior to addition to host cells Viral-induced foci per culture | Pre-incubated with host cells prior to addition to virus Viral-induced foci per culture |
| 0 | 240 | 240 |
|   | 196 | 196 |
| 1.6 | 196 | 53 |
|   | 168 | 13 |
| 8.0 | 60 | 5 |
|   | 124 | 3 |
| 40 | 116 | 0 |
|   | 104 | 0 |
| 200 | 34 | 0 |
|   | 42 | 0 |

Complete inhibition was seen at 40 µg/ml only when cellulose sulfate was pre-incubated with host cells, although partial inhibition was noted at that dose level when mixed first with the virus. At 200 ug/ml, almost complete inhibition of infection was obtained when cellulose sulfate was pre-incubated with the virus before addition to the host cells. These results show that cellulose sulfate inhibits infection both when added first to the virus or first to the host cells although it tends to be somewhat more effective when added first to the host cells.

In a similar study using the BPV-1 focus forming assay, the effect of the cellulose sulfate and dextran sulfate on BPV was tested. In this study, cellulose sulfate tested was as described above. Dextran sulfate used was from Dextran Products Limited (Lot DSM—122) prepared using dextran of average $M_r$ of about 500,000 (based on viscosity) and is estimated to have a final average greater than about 500,000 and may be about 1 to 1.1 million.

Microbicidal activity of the compounds was tested using the well-characterized BPV-1 focus-forming assay (Dvoretzky, I., R. Shober, S. K. Chattopadhyay, and D. R. Lowy. 1980. *A quantitative in vitro focus assay for bovine papilloma virus*. Virology 103:369-375), with modifications for microbicide testing (Hermonat, P. L., (1992) supra; Howett, M. K., et al. (1999) supra. The terms inhibiting or microbicidal activity when used are intended to refer broadly to microbe infection and/or microbe inactivating effect.

Aliquots of BPV-1 containing approximately 100-200 focus-forming units were preincubated with dilutions of compounds for 10 min at 37° C. prior to addition to cultures of mouse C127 cells. Cultures of C127 cells were set up in T25 tissue culture flasks (Corning, New York), containing $3\times10^5$ cells per flask. Virus-compound mixtures in a total of 50 µl were then added to flasks in 1 ml of media, and an additional 3 ml of media added after 24 hrs culture. Media was changed every 3-4 days for a period of 2 weeks. Foci were enumerated following staining of the monolayer with crystal violet and counting stained foci microscopically. Each concentration of compound was tested in duplicate, and the mean±SD of foci number for the preincubation virus-drug concentration for each compound is shown below as Table C.

TABLE C

Inhibitory effect of cellulose sulfate and dextran sulfate when mixed with the bovine papilloma virus before addition of the mixture to host cells

| | Average ± standard deviation (% of control) | | | |
|---|---|---|---|---|
| | Cellulose sulfate | | Dextran sulfate | |
| Concentration (µg/ml) | C127 cell line | C127-D10 clone | C127 cell line | C127-D10 clone |
| 0 (control) | 100 | 100 | 100 | 100 |
| 0.01 | 80 ± 12 | 73 ± 31 | 81 ± 3 | 64 ± 8.0 |
| 0.1 | 76 ± 9 | 80 ± 16 | 102 ± 10 | 83 ± 16 |
| 1 | 73 ± 5 | 33 ± 3 | 97 ± 7 | 69 ± 7 |
| 10 | 42 ± 3 | 3 ± 3 | 113 ± 2 | 3 ± 3 |
| 100 | 10 ± 2 | 2 ± 3 | 43 ± 7 | 3 ± 3 |
| 1,000 | 0 | 0 | 6 ± 3 | 0 |
| 10,000 | 0 | 0 | 0 | 0 |

Microbicidal activity of compounds was also tested by pre-incubation of cells with compounds followed by addition of virus to compound-coated C127 cells. In these experiments, dilutions of compounds were added to cultures of C127 cells, incubated for 1 hr at 37° C., washed 3 times with media to remove unbound compound, prior to addition of approximately 100 focus-forming units of BPV-1. The cultures were incubated for an additional hour, washed three times to remove unbound virus, then the incubation was continued for two weeks with media changes every 3-4 days and foci counted as described above. The results are shown below in Table D.

TABLE D

Inhibitory effect of cellulose sulfate and dextran sulfate when mixed with target cells, followed by washing of the cells and addition of the bovine papilloma virus

| | Average ± standard deviation (foci/well) | |
|---|---|---|
| Concentration (µg/ml) | Cellulose sulfate | Dextran sulfate |
| 0 | 88 ± 15.6 | 115 (n = 1) |
| 10 | 103 ± 6.3 | 31 ± 16.9 |
| 100 | 120 ± 8.4 | 15 ± 4.6 |
| 1,000 | 87 ± 45.1 | 4 ± 2.6 |
| 10,000 | 2 ± 1.3 | 0 |

The results from Table C demonstrated that both compounds showed microbicidal activity against BPV-1. From 10 to 100 µg/ml CS showed moderate to high inhibition of papilloma virus infectivity using the C127 cell line, with complete inhibition at 1 mg/ml. DS showed moderate inhibition at 100 µg/ml and very high inhibition at 1 mg/ml. Clones were derived from the parental C127 cell line because of the consistent failure of BPV-1 to induce foci following several cell passages of the uncloned parental cell line. One clone, labeled C127-D10, which produced foci upon BPV-1 infection, was chosen for a repeat testing of the compounds. When this clone was tested for microbicidal activity, less compound was required to achieve high reduction in BPV-1-induced foci when compared to the uncloned parental-C127 cells.

Pre-incubation of C127-D10 cells with compounds prior to addition of BPV-1 was tested to determine whether the microbicidal effects of CS and DS extended to a blockage of virus interaction with cell surfaces. In these experiments, titrations of compounds were added to cell cultures followed by washing away unbound reagent prior to addition of virus. After a one-hour incubation with virus, unbound virus was removed by washing and the cultures monitored for foci after two weeks.

The results (Table D) indicated that these reagents showed some interference of virus with host cell surfaces as evidenced by a dose-dependent reduction of BPV-1-induced foci. DS showed stronger interference, with substantial reduction in foci at doses of 10 µg/ml. In contrast, CS showed only weak microbicidal effects when C127-D10 cells were pre-treated with this compound except at a concentration of 10 mg/ml. The difference in the results seen with the earlier study is likely due to the fact that in the earlier study, unbound cellulose sulfate was not washed away prior to addition of virus. Since cellulose sulfate or other sulfated polysaccharide upon administration, for example, vaginally should remain in the vaginal cavity, the earlier results more likely represents in vivo effects and the compound in vivo is expected to inactivate papilloma virus both by direct association and by interfering with virus attachment to cells.

EXAMPLE 2

Inhibition of Human Papilloma Virus (HPV)

Cellulose sulfate and dextran sulfate were each prepared as a 2 mg/ml solution in 0.9% NaCl and tested for microbicidal activity using the in vitro HPV transient infection assay originally described by Smith and colleagues (Smith, L. H., C. Foster, M. E. Hitchcock, and R. Isseroff. 1993. *In vitro HPV-11 infection of human foreskin. J. Invest. Dermatol.* 101:292-295) with some modifications (Ludmerer, S. W., W. L. McClements, X. M. Wang, J. C. Ling, K. U. Jansen, and N. D. Christensen. 2000. *HPV11 mutant virus-like particles elicit immune responses that neutralize virus and delineate a novel neutralizing domain. Virology* 266: 237-245). An ELISA-based read-out of Optical Density (OD) values using alkaline phosphatase cleavage of the substrate p-nitrophenyl phosphate was also used to measure HPV infection as described below.

In the standard RT-PCR assay (Ludmerer, S. W., et al. supra; Smith, L. H., et al. supra; Smith, L. H., C. Foster, M. E. Hitchcock, G. S. Leiserowitz, K. Hall, R. Isseroff, N. D. Christensen, and J. W. Kreider. 1995. *Titration of HPV-11 infectivity and antibody neutralization can be measured in vitro. J. Invest. Dermatol.* 105:438-444) for detection of HPV-11 infection, aliquots of HPV-11 (10 µl) were preincubated with dilutions of compounds (40 µl) for 30 min at 37° C. then the mixtures were added to cultures of human A431 cells. Replicate cultures of A431 cells were set up by plating $5 \times 10^5$ cells (in 1 ml tissue culture medium) per well into 6-well culture plates. Virus-compound mixtures were added to individual A431 cultures and the cultures were incubated for a further 4 days (after overnight incubation, an additional 2 ml of culture medium was added to each culture). Cells were harvested in 1 ml Trizol (GIBCO/BRL), then total RNA prepared for RT and production of viral cDNA from spliced viral transcripts spanning a major splice site between E1 and E4 (Ludmerer, S. W. et al. supra; Smith, L. H. et al. supra). Two rounds of PCR amplification using nested primers prepared from the published sequence were conducted for detection of the spliced viral transcript, and the PCR products were detected as ethidium-stained bands on agarose gels (Ludmerer, S. W. et al. supra; Smith, L. H. et al. supra). PCR products were cloned and sequenced to confirm the viral origin of the PCR product. The presence of the correct sized viral PCR product was used to confirm successful infection by HPV-11, as well as a failure to inactivate and/or block the virus by the test compound. In contrast, the lack of a viral PCR product was interpreted to indicate virus inactivation, and/or a failure of the virus to infect A431 cells. Amplified β-actin transcripts (Smith, L. H., et al. supra) were used as a control to establish the integrity of RNA isolation and RT-PCR procedures for uninfected cells and for cultures in which BPV-11 inactivation was achieved.

The RT-PCR assay to detect HPV-40 infection was designed similarly for the detection of HPV-11 infection as described above.

A modification of the RT-PCR assay that incorporates an ELISA-based read-out (Boehringer-Mannheim) was also included to assess microbicidal activity. Replicate cell cultures of A431 cells were infected with an aliquot of infectious HPV virions as described above. After 4 days of culture, cells were harvested and RNA extracted RNA was subjected to RT using downstream anti-sense (reverse) primers for HPV-11 or HPV-40 and β-actin (as a control/housekeeping cellular transcript) to initiate cDNA synthesis. The cDNA was processed through 2 sets of 30 cycles of PCR amplification using nested primers: the second set of cycles used digoxygenin (DIG)-dUTP to label the PCR products with DIG. DIG-labeled PCR products were denatured then renatured together with a biotinylated oligonucleotide specific for the targeted PCR product. Biotinylated products were detected in ELISA with plates coated with streptavidin (to capture the biotinylated target PCR product) then anti-DIG antibody and substrate. Labeled PCR products were added directly to ELISA plates, or titrated at 10-fold dilutions in duplicate for each cell culture for each virus dilution.

TABLE E

ELISA RT-PCR detection of transient infection of HPV-11 and HPV-40.

| Cell culture conditions[a] | Concentration of PCR products[b] | Mean (SD) of ELISA O.D. readings | |
|---|---|---|---|
| | | HPV-11 probe | HPV-40 probe |
| HPV-11 infection | 10 | 1.827 (0.174) | −0.013 (0.000) |
| | 1 | 1.540 (0.034) | NT[c] |
| | 0.1 | 0.845 (0.039) | NT |
| HPV-40 infection | 10 | 0.012 (0.002) | 2.000 (0.000) |
| | 1 | NT | 1.842 (0.080) |
| | 0.1 | NT | 1.027 (0.028) |

[a]A431 cultures infected with either HPV-11 or HPV-40.
[b]Volume (μl) of reaction products from the second set of PCR amplification products added to the ELISA wells.
[c]Not tested.

TABLE F

RT-PCR ELISA for detection of transient infection of human A431 cells with HPV-11 or HPV-40.[a]

| Compound (μg/ml at viral pretreatment dose) | Mean (SD) of O.D. reading for RT-PCR ELISA | |
|---|---|---|
| | HPV-11 probe | β-actin probe |
| Experiment #1[b] | | |
| Cells alone | 0.043 (0.004) | 1.645 (0.052) |
| HPV-11 only | 1.417 (0.063) | 1.564 (0.051) |
| CS 1000 μg/ml (no virus) | 0.028 (0.004) | 1.427 (0.013) |
| DS 1000 μg/ml (no virus) | 0.000 (0.000) | 1.470 (0.001) |
| [c]CS 100 μg/ml | 0.038 (0.001) | 1.518 (0.020) |
| [c]CS 100 μg/ml | 0.049 (0.001) | 1.532 (0.025) |
| [c]CS 10 μg/ml | 1.485 (0.045) | 1.576 (0.021) |
| [c]DS 100 μg/ml | 0.035 (0.000) | 1.583 (0.022) |
| [c]DS 10 μg/ml | 0.023 (0.000) | 1.636 (0.105) |
| | HPV-40 probe | β-actin probe |
| Experiment #2[d] | | |
| [c]CS 1000 μg/ml | 0.037 (0.004) | N.D.[e] |
| [c]CS 100 μg/ml | 0.128 (0.008) | N.D. |
| [c]CS 10 μg/ml | 0.397 (0.050) | N.D. |
| [c]DS 1000 μg/ml | 0.006 (0.007) | N.D. |
| [c]DS 100 μg/ml | 0.375 (0.073) | N.D. |
| [c]DS 10 μg/ml | 0.042 (0.007) | N.D. |
| HPV-40 only | 1.320 (0.0.74) | N.D. |

[a]Two additional experiments yielded similar results.
[b]Infected with HPV-11.
[c]With virus.
[d]Infected with HPV-40.
[e]Not determined.

The microbicidal activity was assessed either as the detection of ethidium stained PCR products or as an ELISA-based readout as described above. Virus inactivation or lack of virus infection was evidenced by the failure to detect viral spliced RT-PCR products (results not shown) and/or the lack of ELISA values above background when using the ELISA assay to detect labeled PCR products. An initial experiment was conducted to test the specificity of the ELISA-based RT-PCR assay using HPV-11 and HPV40 infection of A431 cells (Table E). Highly specific detection of either HPV-11 or 40 was observed by the presence of high ELISA O.D. values for the HPV-11 probe from BPV-11-infected but not HPV-40-infected cultures and vice versa.

Both compounds demonstrated strong microbicidal activity against both HPV-11 and -40 in both tests and representative experiments using RT-PCT Elisa are summarized in Table F. The results showed that RT-PCR products from cells alone or from uninfected cultures treated with compounds consistently demonstrated low O.D. readings in the ELISA assay for the HPV products and high O.D. readings for the β-actin product. Upon HPV-11 and/or HPV-40 infection, cultures showed high levels of ELISA detectable viral products, and addition of microbicides decreased the signal back to background (uninfected) levels. For CS, this occurred at 100 and 1000 μg/ml, and for DS at 10 and 100 μg/ml when tested for microbicidal activity against HPV-11. In assays for HPV-40 infectivity, CS was microbicidal at 100 and 1000 μg/ml and DS at 10 and 1000 μg/ml. There was no cellular cytotoxicity for any of the doses of compounds as determined by microscopic examination of the cell cultures.

Cellulose sulfate (CS) described in Example 1 was tested in each of the following examples.

EXAMPLE 3

Inhibition of Trichomonas by Cellulose Sulfate

The inhibitory effect of CS on trichomonas vaginalis, protozoa known to cause vaginitis, is shown below. The organisms were grown in modified Diamond's medium. CS was mixed with the organism in modified Diamond's medium at a final concentration of about 5 mg/ml (5.12 mg/ml) and incubated anaerobically at 35° C. Samples were collected at various time points and the number of live trichomonas counted with a hemacytomer. The same procedure was performed in the absence of CS. The volume of the inoculum was varied as indicated in the Tables to study the effect of increasing amounts of the organism on the results.

TABLE G

Control

| Incubation time | 400 µl Trich | 200 µl Trich | 100 µl Trich | 50 µl Trich |
|---|---|---|---|---|
| 16 hr | 260 | 130 | 55 | 25 |
| 24 hr | 620 | 210 | 100 | 60 |
| 40 hr | Tntc | 850 | 360 | 130 |
| 48 hr | Tntc | tntc | 500 | 250 |

Numbers indicate the number of life organisms per ml
Trich = Trichomonas
Tntc = too numerous to count

TABLE H 5 mg/ml Cellulose Sulfate

| Incubation time | 400 µl Trich | 200 µl Trich | 100 µl Trich | 50 µl Trich |
|---|---|---|---|---|
| 16 hr | 0 | 0 | 0 | 0 |
| 24 hr | 0 | 0 | 0 | 0 |
| 40 hr | 0 | 0 | 0 | 0 |
| 48 hr | 0 | 0 | 0 | 0 |

Complete inhibition of growth of the trichomonas culture was observed when mixed with 5 mg/ml CS.

A sulfated polysaccharide such as cellulose sulfate, therefore may be used to prevent, inhibit or treat parasitic infection such as by *Trichomonas vaginalis* and by *Enterobius vermicularis* also known to cause vaginitis and related parasites.

EXAMPLE 4

Inhibition of Fungal, Yeast and Bacterial Growth

6% CS was prepared in water as a translucent gel. Twenty grams of the gel was placed in a plastic screw-cap centrifuge tube. The microbial inoculants were prepared, gently vortexed and 0.1 ml inoculant was aseptically pipetted into the 20.0 gram gel. This procedure was repeated for each microbial organism. The samples were incubated at room temperature (20-25° C.) for 14 days or 28 days. The microbes tested and their theoretical yields can be found in Table F. After 14 or 28 days incubation, dilutions ($10^{-1}$, $10^{-2}$, $10^{-3}$) of the gels were made in saline and 1 ml plated onto Sabouraud dextrose (*Aspergillus* and *Candida*) or onto tryptic soy (other microbes). The number of organisms that grew after 3-7 days at room temperature were counted.

TABLE I

| Test Organism | ATCC # | Theoretical* Yield CFU/g | Day 14 CFU/g | Day 28 CFU/g |
|---|---|---|---|---|
| *Aspergillus niger* | 16404 | $2.3 \times 10^5$ | 0 | 0 |
| *Candida albicans* | 10231 | $4.5 \times 10^5$ | 0 | 0 |
| *Staphylococcus aureus* | 6538 | $1.2 \times 10^5$ | 0 | 0 |
| *Eschericia coli* | 8739 | $2.0 \times 10^5$ | 0 | 0 |
| *Pseudomonas aeruginosa* | 9027 | $3.0 \times 10^5$ | 0 | 0 |

*Theoretical yield = CFU/ml × amount of inoculant (.1 ml)/amount of sodium cellulose sulfate gel (20 g)

The results shows surprisingly that CS inhibits fungal and yeast infections, including *Candida* which is associated with vaginitis. CS previously shown to inhibit *N. gonorrhea* and *C. trachomatis* infections also showed inhibition of bacteria *S. aureus*, *E. coli* and *P. aeruginosa*.

In another study, CS was dissolved in water at the concentrations indicated below. No other ingredients, including preservatives, were added. The gels were challenged with microbes as described above except that the gels were examined for the presence of microbes after 1, 2, 3, 4 and 7 days. The results were as follows. The amount of microbes originally inoculated in the gels is also shown below.

| *Asperigillus niger* (CFU × $10^5$/ml) | | | | | |
|---|---|---|---|---|---|
| CS % | 24 hours | 48 hours | 72 hours | 96 hours | 7 days |
| 0.06 | 0 | 0 | 0 | 0 | 0 |
| 0.6 | 0 | 0 | 0 | 0 | 0 |
| 1.2 | 0 | 0 | 0 | 0 | 0 |
| 6 | 0 | 0 | 0 | 0 | 0 |

CS gel in as low a concentration as 0.6% completely inactivated *Asperigillus*.

| *Candida albicans* (CFU × $10^5$/ml) | | | | | |
|---|---|---|---|---|---|
| CS % | 24 hours | 48 hours | 72 hours | 96 hours | 7 days |
| 0.06 | 0 | 0 | 0 | 0 | 0 |
| 0.6 | 0 | 0 | 0.62 | 0.655 | 0.535 |
| 1.2 | 0 | 0 | 0 | 0 | 0 |
| 6 | 0 | 0 | 0 | 0 | 0 |

CS gel in as low a concentration as 0.6% inactivated *Candida*. Complete inactivation was obtained at 1.2 and 6%.

| *Staphylococcus aureus* (CFU × $10^5$/ml) | | | | | |
|---|---|---|---|---|---|
| CS % | 24 hours | 48 hours | 72 hours | 96 hours | 7 days |
| 0.06 | 0.625 | 0.715 | 1.04 | 2.06 | 5.815 |
| 0.6 | 5.17 | 5.53 | 4.82 | 6.41 | 3.25 |
| 1.2 | 2.71 | 4.725 | 2.39 | 3.96 | 3.55 |
| 6 | 0 | 0.005 | 0 | 0 | 0 |

6% CS gel completely inactivated *Staphyloccus*. At lower CS concentrations, the microbe was not inactivated but growth was prevented. The 0.06% CS gel initially inactivated most *Staphylococcus* (in contrast to the 0.6% and 1.2% gels) but allowed slow growth thereafter.

| *Escherichia coli* (CFU × $10^5$/ml) | | | | | |
|---|---|---|---|---|---|
| CS % | 24 hours | 48 hours | 72 hours | 96 hours | 7 days |
| 0.06 | 0 | 1.15 | 1.21 | 0.13 | 1.12 |
| 0.6 | 5.6 | 5.81 | 4.43 | 6.92 | 4.39 |
| 1.2 | 0.98 | 3.125 | 1.625 | 4.54 | 3.78 |
| 6 | 0 | 0.01 | 0 | 0 | 0 |

6% CS gel completely inactivated *Escherichia*. At lower CS concentrations, the microbe was either not inactivated or only to a minor extent (except by the 0.06% CS gel) but no growth occurs.

| | *Pseudomans aeruginosa* (CFU × $10^5$/ml) | | | | |
|---|---|---|---|---|---|
| CS % | 24 hours | 48 hours | 72 hours | 96 hours | 7 days |
| 0.06 | 0 | 0.48 | 1.125 | 1.87 | 2.04 |
| 0.6 | 5.43 | 6.80 | 4.43 | 6.92 | 6.05 |
| 1.2 | 2.08 | 2.625 | 2.31 | 2.82 | 4.79 |
| 6 | 0 | 0 | 0 | 0 | 0 |

6% CS gel completely inactivated *Pseudomonas*. At lower CS concentrations, the microbe was not inactivated but growth was prevented. The 0.06% CS gel initially inactivated most *Staphylococcus* (in contrast to the 0.6% and 1.2% gels) but allowed slow growth thereafter.

| Original inoculum (CFU × $10^5$/ml) | |
|---|---|
| *Asperigillus niger* | 2.25 |
| *Candida albicans* | 4.55 |
| *Staphylococcus aureus* | 3.78 |
| *Escherichia coli* | 5.98 |
| *Pseudomonas aeruginosa* | 2.23 |

A sulfated polysaccharide, such as cellulose sulfate therefore may be used to prevent, inhibit or treat fungal infections, such as by *Candida* and *Asperigillus*, *Trichophyton*, *Epidernophyton* and *Microsporum*, including *C. albicans*, *A. niger*, *T. pedis*, *T. cruris* and *T. capitis* and related fungal infections.

EXAMPLE 6

Experimental Procedures

A. Broth Method

CS was serially diluted in brucella broth supplemented with laked sheep blood, vitamin K, and hemin (highest concentration tested was 10 mg/ml). Aliquots (1 ml) of the mixtures were then added to 12×75 mm plastic tubes. Test strains were suspended in each of the tubes to a turbidity equal to the ½ McFarland Standard in supplemented brucella broth and diluted about 1:50 in brucella broth to obtain a concentration of about 3×$10^6$ CFU/ml. Samples (1 ml) of the test strains were added to the CS dilution series and then incubated for 2 days at 37° C. under anaerobic conditions. Tubes containing no organism or no drug were tested simultaneously as negative and positive controls. For each organism tested, the lowest concentration of CS that completely inhibited growth (MIC) was determined.

B. Agar Method

Various concentrations of cellulose sulfate in water (highest concentration tested was 0.625 mg/ml) were mixed with molten brucella agar supplemented with sheep blood, vitamin K, and hemin (NCCLS reference agar dilution method) and then poured into separate plates. After the plates were solidified and dried, suspensions of the test organisms ($10^8$ CFU/ml) were spotted on the surface using a replicating device that delivered a final concentration of $10^5$ CFU/spot. After incubation at 37° C. for 48 hours under anaerobic conditions, the plates were examined for growth. For each organism tested, the lowest concentration of CS that completely inhibited growth (MIC) as compared to the drug free growth control plate was determined.

Results

The results are shown in Table J. At the time the agar method was used, only concentrations up to 0.625 mg/ml of cellulose sulfate were tested so that the agar method results are limited. The broth method may represent a better indicator of activity because the movement of large molecules is more restricted in agar.

In the broth method, CS inhibited both strains of *Fusobacterium nucleatum* and both strains of *Fusobacterium gonidiaformans*.

Neither one of the strains of *Prevotella melaninogenica* were inhibited at the concentrations tested. However, all strains of *Prevotella intermedia*, *Prevotella bivia* and *Prevotella disiens* were inhibited by CS.

Two strains of *Porphyromonas asaccharolytica* were inhibited but a third one was not at the concentrations tested. Both strains of *Porphyromonas levii* were inhibited.

CS inhibited both strains of *Gardnerella vaginalis*.

All strains of *Peptostreptococcus magnus*, *Peptostreptococcus tetradius* and *Peptostreptococcus asaccharolyticus* were inhibited by CS.

Both strains of *Eubacterium lentum* were inhibited.

CS inhibited one strain of *Clostridium perfringes* but not another one at the concentrations tested.

One strain of *Bacteroides thetaiotaomicron* was inhibited but three others were not at the concentrations tested. Similarly, one strain of *Bacteroides fragilis* was inhibited but three others were not at the concentrations tested.

TABLE J

INHIBITION OF BV-CAUSING MICROBES BY CELLULOSE SULFATE (LOT 80971)

| rma# | Organism | Broth (study 1) CS MIC (mg/ml) | Broth (study 2) CS MIC (mg/ml) | Agar* CS MIC (mg/ml) |
|---|---|---|---|---|
| 10481 | *F. nucleatum* | | 5 | >0.625** |
| 11518 | *F. nucleatum* | | 10 | >0.625 |
| 11423 | *F. gonidiaformans* | | 5 | >0.625 |
| 11653 | *F. gonidiaformans* | | 5 | 0.156 |
| 9052 | *Prev. melaninogenica* | | NI | >0.625 |
| 5657 | *Prev. melaninogenica* | | NI | >0.625 |
| 11142 | *Prev. intermedia* | | 10 | >0.625 |
| 11168 | *Prev. intermedia* | | 10 | >0.625 |
| 11697 | *Prev. bivia* | 0.6 | 5 | >0.625 |
| 11683 | *Prev. bivia* | NI | 5 | >0.625 |
| 11579 | *Prev. disiens* | | 10 | >0.625 |
| 11698 | *Prev. disiens* | | 10 | >0.625 |
| 11690 | *Porph. asacch.* | | NI | |
| 11656 | *Porph. asacch.* | | 5 | >0.625 |
| 11612 | *Porph. asacch.* | | | 0.08 |
| 11425 | *Porph. levii* | 0.6 | 0.6 | >0.625 |
| 11601 | *Porph. levii* | 0.3 | 0.3 | 0.04 |
| 12066 | *Gard. vaginalis* | | 5 | |
| 12262 | *Gard. vaginalis* | | 5 | |
| 11658 | *Ps. Magnus* | | 5 | >0.625** |
| 11598 | *Ps. Magnus* | | 5 | >0.625 |
| 11287 | *Ps. Tetradius* | | 5 | >0.625 |
| 11253 | *Ps. Tetradius* | | 5 | >0.625 |
| 11587 | *Ps. Asacch.* | | 10 | >0.625 |
| 11607 | *Ps. Asacch.* | | 10 | >0.625 |
| 9420 | *Eubact. Lentum* | | 5 | >0.625 |
| 11700 | *Eubact. Lentum* | | 10 | >0.625 |

TABLE J-continued

INHIBITION OF BV-CAUSING MICROBES BY CELLULOSE SULFATE (LOT 80971)

| rma# | Organism | Broth (study 1) CS MIC (mg/ml) | Broth (study 2) CS MIC (mg/ml) | Agar* CS MIC (mg/ml) |
|---|---|---|---|---|
| 11608 | Clost. Perfringes | | 10 | >0.625 |
| 11655 | Clost. Perfringes | | NI | >0.625 |
| ATCC | B. theta | NI | NI | >0.625 |
| ATCC | B. theta | | 10 | |
| 11604 | B. theta | | NI | >0.625 |
| 11651 | B. theta | | NI | >0.625 |
| ATCC | B. fragilis | NI | 10 | >0.625 |
| ATCC | B. fragilis | | NI | |
| 11647 | B. fragilis | | NI | >0.625 |
| 11652 | B. fragilis | | NI | >0.625 |

*Only concentrations of 0.6 mg/ml or less were tested in agar
**i.e. No effect concentration up to 0.625 mg/ml
NI for the broth method = not inhibited by 10 mg/ml (the highest concentration tested)
NI = not inhibited by 10 mg/ml (the highest concentration tested)
Blank = not tested
MICROBES TESTED (see Tables)
F. nucleatum = Fusobacterium nucleatum
F. gonidiaformans = Fusobacterium gonidiaformans
Prev. melaninogenica = Prevotella melaninogenica
Prev. intermedia = Prevotella intermedia
Prev. bivia = Prevotella bivia
Prev. disiens = Prevotella disiens
Porph. asacch. = Porphyromonas asaccharolytica
Porph levii = Porphyromonas levii
Gard. vaginalis = Gardnerella vaginalis
Ps. magnus = Peptostreptococcus magnus
Ps. tetradius = Peptostreptococcus tetradius
Ps. asacch. = Peptostreptococcus asaccharolyticus
Eubact. lentum = Eubacterium lentum
Clost. perfringes = and Clostridium perfringes
B. theta = Bacteroides thetaiotaomicron
B. fragilis = Bacteroides fragilis

EXAMPLE 7

Inhibition of Gardnerella vaginalis

A fresh subculture of G. Vaginalis which is bacteria frequently associated with vaginitis was obtained after overnight growth (16 hours) on a V-agar plate and suspended in sterile phosphate buffered saline (PBS; pH 7.2) to achieve a turbidity of 0.5 (McFarland standard; approximately 108 CFU/ml). The suspension was diluted 10 fold and applied to HBT bilayer agar plates by swabbing the entire plate. The plate was allowed to dry for 2-3 min and small wells punched in the agar, 10 mm in diameter. Samples of cellulose sulfate were dissolved at 10 mg/ml in PBS and 0.2 ml placed in the agar wells. As control, 0.2 ml PBS was placed in one of the wells. Growth inhibition was indicated by a light area around the well. No growth inhibition was observed with PBS, whereas an area of 6 mm in diameter was found around the cellulose sulfate well, showing growth inhibition.

The studies were repeated using various concentrations of cellulose sulfate (ranging from 10 mg/ml to 0.125 mg/ml) and 4 different Gardnerella vaginalis strains. Dose dependent inhibition of each strain was observed. The lowest initial concentration of cellulose sulfate at which growth inhibition occurred was 0.5 mg/ml.

EXAMPLE 8

Inhibition of Vaginosis-Causing Bacteria

In another study, cellulose sulfate was prepared at a variety of concentrations in water (highest tested was 625 µg/ml) and mixed with molten brucella agar supplemented with sheep blood, vitamin K and hemin. After the plates were poured and dried, suspensions of the test strains were prepared and applied to the surface of the plates at a final concentration of 100,000 CFU per spot. After incubation for 48 hours in an anaerobic environment, the plates were examined for growth and the lowest concentration of compound that inhibited growth determined.

Inhibition of the Following Organisms was Observed:
1. Fusobacterium gonidadormans—inhibited at 156 µg/ml and higher
2. Porphyromonas asacch—inhibited at 80 µg/ml and higher
3. Porphyromonas levii—inhibited at 40 µg/ml and higher All references cited herein are fully incorporated by reference. Having now described the invention, it will be understood by those skilled in the art that various modifications can be made to the described embodiments without departing from the scope and spirit of the invention. Such modifications are intended to be within the scope of the invention.

We claim:

1. A method of treating fungal infection in a subject in need of such treatment comprising administering an effective amount of a sulfated polysaccharide, wherein the sulfated polysaccharide is cellulose sulfate, dextran sulfate, dermatan sulfate, chondroitin sulfate, pentosan sulfate, fucoidin, mannan sulfate, dextrin sulfate, curdlan sulfate, chitin sulfate, heparin or heparin sulfate.

2. The method according to claim 1 wherein the subject is a human patient.

3. The method according to claim 2 wherein the sulfated polysaccharide is cellulose sulfate.

4. The method according to claim 3 wherein the fungal infection is Asperigillus infection or Candida infection.

5. The method according to claim 4 wherein the fungal infection is Asperigillus niger infection or Candida albicans infections.

6. The method according to claim 5 wherein sulfation of cellulose is at least 12%.

7. The method according to claim 6 wherein cellulose sulfate is maximally sulfated.

8. The method according to claim 5 wherein cellulose sulfate has an average molecular weight (Mr) greater than about 500,000 daltons.

9. The method according to claim 8 wherein cellulose sulfate has an average Mr of about 1-2 million daltons.

10. The method according to claim 5 wherein the effective amount is about 0.1 to 200 mg/ml.

11. The method according to claim 10 wherein the effective amount is about 1 to 100 mg/ml.

12. The method according to claim 11 wherein the effective amount is about 50 to 100 mg/ml.

13. The method according to claim 5 wherein cellulose sulfate is administered in combination with a pharmaceutically acceptable carrier or diluent.

14. The method according to claim 13 wherein cellulose sulfate is administered topically.

15. The method according to claim 13 wherein cellulose sulfate is administered vaginally.

16. A method of inhibiting fungal infection in a subject in need of such inhibition comprising administering an effective amount of a sulfated polysaccharide, wherein the sulfated polysaccharide is cellulose sulfate, dextran sulfate, dermatan sulfate, chondroitin sulfate, pentosan sulfate, fucoidin, mannan sulfate, dextrin sulfate, curdlan sulfate, chitin sulfate, heparin or heparin sulfate.

17. The method according to claim 16 wherein the subject is a human patient.

18. The method according to claim 17 wherein the sulfated polysaccharide is cellulose sulfate.

19. The method according to claim 18 wherein the fungal infection is *Asperigillus* infection or *Candida* infection.

20. The method according to claim 19 wherein the fungal infection is *Asperigillus niger* infection or *Candida albicans* infections.

21. The method according to claim 20 wherein sulfation of cellulose is at least 12%.

22. The method according to claim 21 wherein cellulose sulfate is maximally sulfated.

23. The method according to claim 20 wherein cellulose sulfate has an average molecular weight (Mr) greater than about 500,000 daltons.

24. The method according to claim 23 wherein cellulose sulfate has an average Mr of about 1-2 million daltons.

25. The method according to claim 20 wherein the effective amount is about 0.1 to 200 mg/ml.

26. The method according to claim 25 wherein the effective amount is about 1 to 100 mg/ml.

27. The method according to claim 26 wherein the effective amount is about 50 to 100 mg/ml.

28. The method according to claim 20 wherein cellulose sulfate is administered in combination with a pharmaceutically acceptable carrier or diluent.

29. The method according to claim 28 wherein cellulose sulfate is administered topically.

30. The method according to claim 28 wherein cellulose sulfate is administered vaginally.

* * * * *